(12) United States Patent
Young et al.

(10) Patent No.: US 9,956,396 B2
(45) Date of Patent: May 1, 2018

(54) THIN FILM FOR A LEAD FOR BRAIN APPLICATIONS

(71) Applicant: Medtronic Bakken Research Center B.V., Maastricht (NL)

(72) Inventors: Edward Willem Albert Young, Maastricht (NL); Hoa Thi Mai Pham, Eindhoven (NL); Martinus Lambertus Wilhelmus Vorstenbosch, Lieshout (NL); Ke Wang, Valkenswaard (NL)

(73) Assignee: Medtronic Bakken Research Center B.V., Maastricht (NL)

( * ) Notice: Subject to any disclaimer, the term of this patent is extended or adjusted under 35 U.S.C. 154(b) by 0 days. days.

(21) Appl. No.: 13/762,426

(22) Filed: Feb. 8, 2013

(65) Prior Publication Data

US 2013/0204318 A1    Aug. 8, 2013

Related U.S. Application Data

(60) Provisional application No. 61/596,253, filed on Feb. 8, 2012.

(51) Int. Cl.
| | |
|---|---|
| *A61N 1/00* | (2006.01) |
| *A61N 1/05* | (2006.01) |
| *A61N 1/36* | (2006.01) |
| *H05K 3/10* | (2006.01) |
| *H05K 1/11* | (2006.01) |

(Continued)

(52) U.S. Cl.
CPC ......... *A61N 1/0534* (2013.01); *A61N 1/3606* (2013.01); *H05K 3/108* (2013.01); *A61N 1/05* (2013.01); *A61N 1/36125* (2013.01); *H05K 1/11* (2013.01); *H05K 3/16* (2013.01); *H05K 3/28* (2013.01); *H05K 2203/1322* (2013.01)

(58) Field of Classification Search
CPC .... A61N 1/0534; A61N 1/36125; A61N 1/05; A61N 1/3606; H05K 1/11; H05K 3/108; H05K 2203/1322; H05K 3/28
USPC ...................... 607/45, 46, 116; 600/373, 378
See application file for complete search history.

(56) References Cited

U.S. PATENT DOCUMENTS 4,417,387 A  *  11/1983  Heslop .............. H01L 23/53242
                                                           257/763
5,650,897 A  *   7/1997  Cohen et al. ............ 360/123.37
5,683,442 A  *  11/1997  Davidson ...................... 607/116

(Continued)

FOREIGN PATENT DOCUMENTS

| WO | 99/49934 A1 | 10/1999 |
|---|---|---|
| WO | 2006131912 A2 | 6/2007 |
| WO | 2010055453 A1 | 5/2010 |

OTHER PUBLICATIONS

International Search Report and Written Opinion dated Aug. 8, 2013 for PCT/EP2013/052323.

*Primary Examiner* — Lindsey G Wehrheim
(74) *Attorney, Agent, or Firm* — Shumaker & Sieffert, P.A.

(57) ABSTRACT

A thin film for a lead for brain applications includes at least one section comprising a high conductive metal and a low conductive metal, whereby the low conductive metal is a biocompatible metal and has a lower electrical conductivity than the high conductive metal and whereby the high conductive metal is at least partially encapsulated by the low conductive metal. Furthermore, the present invention relates to a method of manufacturing a thin film for a lead for brain applications and a deep brain stimulation system.

28 Claims, 3 Drawing Sheets

(51) Int. Cl.
*H05K 3/16* (2006.01)
*H05K 3/28* (2006.01)

(56) References Cited

U.S. PATENT DOCUMENTS

| | | |
|---|---|---|
| 6,208,881 B1* | 3/2001 | Champeau .................... 600/374 |
| 6,844,023 B2* | 1/2005 | Schulman et al. ........... 427/2.24 |
| 7,941,202 B2 | 5/2011 | Hetke et al. |
| 8,484,841 B1 | 7/2013 | Burros et al. |
| 8,805,542 B2 | 8/2014 | Tai et al. |
| 2003/0022403 A1* | 1/2003 | Shimoda et al. ............... 438/14 |
| 2005/0077630 A1* | 4/2005 | Kirby .................. H01L 21/2885 257/774 |
| 2008/0058895 A1* | 3/2008 | Ok ........................ A61F 15/001 607/54 |
| 2008/0140152 A1* | 6/2008 | Imran et al. .................... 607/46 |
| 2008/0255439 A1 | 10/2008 | Tang et al. |
| 2010/0331938 A1 | 12/2010 | Sommer et al. |
| 2011/0093052 A1 | 4/2011 | Anderson et al. |
| 2011/0224765 A1 | 9/2011 | Harberts et al. |

* cited by examiner

THIN FILM FOR A LEAD FOR BRAIN APPLICATIONS

CROSS-REFERENCE TO RELATED APPLICATIONS

This application claims the benefit of U.S. Provisional Patent Application No. 61/596,253 filed Feb. 8, 2012 entitled "Thin Film for a Lead for Brain Applications", incorporated by reference herein in its entirety.

BACKGROUND OF THE INVENTION

The present invention relates to a thin film for a lead for brain applications, to a method of manufacturing a thin film for a lead for brain applications and to a deep brain stimulation (DBS) system.

BRIEF SUMMARY OF THE INVENTION

In one embodiment there is a thin film for a lead for brain applications, comprising: at least one section comprising a high conductive metal and a low conductive metal, whereby the low conductive metal is a biocompatible metal and has a lower electrical conductivity than the high conductive metal and whereby the high conductive metal is at least partially encapsulated by the low conductive metal. In one embodiment, the high conductive metal is completely encapsulated by the low conductive metal and/or that the high conductive metal and the low conductive metal are at least partially encapsulated by a ceramic material. In one embodiment, the high conductive metal comprises gold and/or copper and/or aluminium and/or silver or is gold or copper or aluminium or silver. In one embodiment, the low conductive metal comprises platinum and/or titanium and/or titanium nitride or is platinum or titanium or titanium nitride. In one embodiment, the high conductive metal is gold and that the low conductive metal is platinum.

In one embodiment, the ceramic material comprises SiN, SiOX, Si-Carbid and/or Alumina or that the ceramic is SiN, SiOX, Si-Carbid and/or Alumina. In one embodiment, the probe is at least partially encapsulated by a flexible polymer, whereby the flexible polymer is preferably a biocompatible polymer. In one embodiment, the flexible polymer is Parylene or SU-8 or silicone or polyimide or polyurethane. In one embodiment, the flexible polymer completely encapsulates the low conductive metal and/or preferably also completely encapsulates the ceramic material. In one embodiment, an additional layer or pattern is arranged on the low conductive metal, whereby the layer or pattern preferably comprises titanium or consists of titanium.

In another embodiment, there is a method comprising manufacturing a thin film having: at least one section comprising a high conductive metal and a low conductive metal, whereby the low conductive metal is a biocompatible metal and has a lower electrical conductivity than the high conductive metal and whereby the high conductive metal is at least partially encapsulated by the low conductive metal.

In one embodiment, the high conductive metal is completely encapsulated by the low conductive metal and whereby the high conductive metal is gold, and the low conductive metal is platinum and whereby the all sided encapsulation of gold traces is realized by conducting at least the following process steps: sputter depositing a platinum layer; selective gold plating of traces on the platinum layer through resist mask to form traces; patterning of platinum; and platinum electroplating of traces.

In one embodiment, the high conductive metal is completely encapsulated by the low conductive metal and whereby the high conductive metal is gold, and the low conductive metal is platinum and whereby the all sided encapsulation of gold traces is realized by conducting at least the following process steps: sputter depositing of a platinum layer; selective gold plating on the platinum layer through resist mask, preferably with a negative slope, to form traces; sputter deposition of platinum; and patterning of platinum.

In one embodiment, the high conductive metal is completely encapsulated by the low conductive metal and whereby the high conductive metal is gold, and the low conductive metal is platinum and whereby the all sided encapsulation of gold traces is realized by conducting at least the following process steps: sputter depositing of a platinum layer; sputter depositing of gold on the platinum layer and subsequently structure the gold to form traces, preferably with sloped edges; sputter deposition of platinum; and patterning of titanium or platinum.

In another embodiment, there is a deep brain stimulation system comprising at least one lead with a thin film for a lead comprising: at least one section comprising a high conductive metal and a low conductive metal, whereby the low conductive metal is a biocompatible metal and has a lower electrical conductivity than the high conductive metal and whereby the high conductive metal is at least partially encapsulated by the low conductive metal.

BRIEF DESCRIPTION OF THE SEVERAL VIEWS OF THE DRAWINGS

The foregoing summary, as well as the following detailed description of embodiments of the thin film for a lead for brain applications, will be better understood when read in conjunction with the appended drawings of an exemplary embodiment. It should be understood, however, that the invention is not limited to the precise arrangements and instrumentalities shown.

In the drawings.

DETAILED DESCRIPTION OF THE INVENTION

Implantable neurostimulation devices have been used in the past 10 years to treat acute or chronic neurological conditions. Deep brain stimulation (DBS), the mild electrical stimulation of sub-cortical structures, belongs to this category of implantable devices, and has been shown to be therapeutically effective for Parkinson's disease, dystonia, and tremor. New applications of DBS in the domain of psychiatric disorders (e. g. obsessive compulsive disorder, depression) are being researched and show promising results. In existing systems, the probes are connected to an implantable current pulse generator.

Currently, systems are under development with more, smaller electrodes in a technology based on thin film manufacturing. These are based on thin film(s) that are/is fixed on a carrier material to form a lead. These probes will have multiple electrode areas and will enhance the precision to address the appropriate target in the brain and relax the specification of positioning. Meanwhile, undesired side effects due to undesired stimulation of neighboring areas can be minimized.

Thin films for leads that are based on thin film manufacturing are disclosed e.g. by U.S. Patent Application Publication No. 2008/0255439 A1 and have been used in research products in animal studies. These novel systems consist of a lead made from a thin film based on thin technology.

Platinum is a well-accepted metal in medical applications. In particular, deep brain probes are made with platinum wires and distal end metal. However, platinum has a relatively limited electrical conductivity. This poses problems in leads based on thin film manufacturing. As the thin film traces are relatively thin and long in these novel thin film based leads, the electrical resistance of pure platinum traces can be substantial. In particular in thin film designs for wound leads for magnetic resonance (MR) compatibility, as e.g. disclosed in U.S. Patent Application Publication No. 2011/224765 A1, the long length of the thin film on the lead would give rise to unacceptably high driving voltages. Additionally, the resistivity of the traces in a thin film should be kept low, typically below 1 to 2 kOhm, to avoid power losses that negatively influence the battery life. However, the traces on the film are narrow.

The materials choice is restricted. Of the accepted metals, platinum as one of few metal or metal alloys has a reasonable conductivity. But in long, narrow, multi trace leads, the resistivity of the traces is a serious concern. The use of thicker platinum layers is not advisable. Thick platinum layers are difficult to handle and process. Therefore, increasing the thickness of the platinum layer to reduce the resistivity of the traces is not a viable option. The use of thicker platinum traces is not feasible. Thick platinum introduces stresses in the thin film and gives rise to pronounced topology on the thin film. Moreover, thick metal limits the bending radius of the thin film probe as materials on top will be stretched.

It is therefore, in some embodiments, an object of the present invention to provide a thin film for a lead for brain applications having an improved electrical conductivity together with good biocompatible characteristics, in particular to improve the resistivity of the probe, but without compromising on the compatibility of the metal system of the probe.

The above object is solved according to the present invention, in some embodiments, by a thin film for a lead for brain applications comprising at least one section with a high conductive metal and a low conductive metal, whereby the low conductive metal is a biocompatible metal and has a lower electrical conductivity than the high conductive metal and whereby the high conductive metal is at least partially encapsulated by the low conductive metal.

Consequently, the advantage is achieved that the biocompatibility of the metal system of the probe comprising the high conductive metal and a low conductive metal is not compromised and that the resistivity of the probe is improved. Further advantageously, the electrical conductivity may be increased by maintaining good biocompatible characteristics of the probe. Furthermore, very good magnetic resonance (MR) compatibility can be achieved because the good electrical conductivity enables the use of relatively long spiralled respectively wound thin film. In these leads, the multi trace lead ribbon is spiralled around a carrier.

A low conductive metal (LCM) is a metal with a relatively low electrical conductivity or a metal alloy with a relatively low electrical conductivity, e.g. with an electrical conductivity $\sigma$ within the range of about $2.00\times10^6$ to $9.75\times10^6$ S/m, especially between $2.38\times10^6$ and $9.43\times10^6$ S/m at 20° C. The electrical resistivity $\rho$ of the low conductive metal (LCM) may be within the range of about $1.00\times10^{-7}$ to $4.50\times10^{-7}$ $\Omega$m at 20° C., especially between $1.06\times10^{-7}$ and $4.20\times10^{-7}$ $\Omega$m at 20° C.

A high conductive metal (HCM) is a metal with a relatively high electrical conductivity or a metal alloy with a relatively high electrical conductivity, e.g. with an electrical conductivity $\sigma$ within the range of about $3.00\times10^7$ to $7.00\times10^7$ S/m, especially between $3.50\times10^7$ and $6.30\times10^7$ S/m at 20° C. The electrical resistivity $\rho$ may be within the range of about $1.50\times10^{-8}$ to $3.00\times10^{-8}$ $\Omega$m at 20° C., especially between $1.59\times10^{-8}$ and $2.82\times10^{-8}$ $\Omega$m at 20° C.

Biocompatible metal means e.g. a metal or metal alloy, which has the ability of a biomaterial to perform its desired function with respect to a medical therapy, without eliciting any undesirable local or systemic effects in the recipient or beneficiary of that therapy, but generating the most appropriate beneficial cellular or tissue response in that specific situation, and optimizing the clinically relevant performance of that therapy. With other words, a biocompatible metal in means e.g. a metal or metal alloy, which is non-toxic to e.g. the brain tissue and/or can be implanted into a human body, preferably into the human brain without or with minor deleterious effects.

The high conductive metal is at least partially outwardly encapsulated by the low conductive metal, so that at least a part of the surface of high conductive metal is covered by the low conductive metal. For example, the surface of high conductive metal can be covered partially by the low conductive metal and furthermore by another material, which is preferably also a biocompatible material.

The lead for brain application is preferably a thin film attached to a carrier.

In a further preferred embodiment the high conductive metal is completely encapsulated by the low conductive metal.

Additionally, it is possible that the high conductive metal and the low conductive metal are at least partially encapsulated by a ceramic material.

Preferably it is possible that the high conductive metal comprises gold and/or copper and/or aluminium and/or silver or is gold or copper or aluminium or silver.

In a further preferred embodiment the low conductive metal comprises platinum and/or titanium and/or titanium nitride or is platinum or titanium or titanium nitride.

In more specific embodiments, a further advantage is that some pair of metals have very good interface adhesion and interdiffusion (i.e. low interdiffusion) properties. For instance, platinum (Pt) and gold (Au) are a good pair. The adhesion of platinum to gold is excellent and inter-diffusion is reported at very high temperatures only and will not compromise the platinum barrier properties and the gold conductivity in the state of the art probe applications probe manufacturing processes. Therefore, platinum is an excellent material to package the gold to prevent gold molecules e.g. from entering the brain tissue. It is therefore preferred that the high conductive metal is gold and that the low conductive metal is platinum.

By this, the further advantage is achieved that the resistivity of e.g. the traces in thin film is improved by introducing a good electrical conductor such as gold as a conductor, but without compromising on the biocompatibility of the metal system by means of preferably an all sided encapsulation of the gold by platinum metal. Thereby and advantageously, low ohmic traces in thin film can be realized by using fully platinum encapsulated gold, which can be of particular importance for wound thin film around a carrier to form a lead. Wounding of a thin film around a carrier is applied to facilitate the bending of the lead and to realize inductance for MR compatibility gives rise to increased length of the cable in order to maintain low resistance in the traces, low Ohmic metallisation on the thin film is required. This embodiment of the present invention enables this advantageously.

In a further preferred embodiment it is possible that the ceramic material comprises SiN, SiOX, Si-Carbid and/or Alumina or that the ceramic is SiN, SiOX, Si-Carbid and/or Alumina.

Preferably, the probe can be at least partially encapsuled by a flexible polymer, whereby the flexible polymer is preferably a biocompatible polymer.

The flexible polymer can be Parylene or epoxy such as SU-8. Alternatively, also silicone, polyimide or polyurethane can be used.

Parylene is a name is for a variety of chemical vapor deposited poly(p-xylylene) polymers used as moisture and dielectric barriers and among these the chosen flexible polymer to be used for the probe can be preferably Parylene-C. Parylene is one of the most biocompatible materials known.

SU-8 is a commonly used epoxy-based negative photoresist. It is a very viscous polymer that can be spun or spread over a thickness ranging from <1 micrometer up to >300 micrometer and still be processed with standard contact lithography. It can be used to pattern high aspect ratio (>20) structures. Its maximum absorption is for ultraviolet light with a wavelength of 365 nm (it is not practical to expose SU-8 with g-line ultraviolet light). When exposed, SU-8's long molecular chains cross-link causing the solidification of the material. SU-8 series photoresists use gamma butyrolactone as the primary solvent.

In a further preferred embodiment it is possible that the flexible polymer is completely encapsulating the low conductive metal and/or preferably also completely encapsulating the ceramic material.

Additionally, an additional layer or pattern can be arranged on the low conductive metal, whereby the layer or pattern preferably comprises titanium or consists of titanium.

Furthermore, the present invention relates to a method of manufacturing a thin film for a lead for brain applications, preferably a thin film for a lead according to any of the claims 1 to 10, the thin film comprising at least one section with a high conductive metal and a low conductive metal, whereby the low conductive metal is a biocompatible metal and has a lower electrical conductivity than the high conductive metal and whereby the high conductive metal is at least partially encapsulated by the low conductive metal.

In a first method option it is possible that the all sided encapsulation of the high conductive metal traces is realized by conducting at least the following process steps:
sputter depositing of a low conductive metal layer;
selective high conductive metal plating of traces on the low conductive metal layer through resist mask to form traces;
patterning of low conductive metal; and
low conductive metal electroplating of traces.

In a further, alternative method option it is possible that the all sided encapsulation of the high conductive metal traces is realized by conducting at least the following process steps:
sputter depositing of a low conductive metal layer;
selective high conductive metal plating on the low conductive metal layer through resist mask, preferably with a negative slope, to form traces;
sputter deposition of low conductive metal; and
patterning of low conductive metal.

It is one preferred option it is possible that the high conductive metal is completely encapsulated by the low conductive metal and whereby the high conductive metal is gold, and the low conductive metal is platinum or titanium and whereby the all sided encapsulation of gold traces is realized by conducting at least the following process steps:
sputter depositing of a platinum layer; a titanium layer may be sputtered prior to the platinum deposition to ensure good adhesion of the platinum;
selective gold plating of traces on the titanium or platinum layer through resist mask to form traces;
patterning of platinum, respectively patterning of titanium and platinum; and
platinum electroplating of traces.

It is another preferred option it is possible that the high conductive metal is completely encapsulated by the low conductive metal and whereby the high conductive metal is gold, and the low conductive metal is platinum or titanium and whereby the all sided encapsulation of gold traces is realized by conducting at least the following process steps:
sputter depositing of a platinum layer; a titanium layer may be sputtered prior to the platinum deposition to ensure good adhesion of the platinum;
selective gold plating on the platinum layer through resist mask, preferably with a negative slope, to form traces;
sputter deposition of platinum; and
patterning of platinum, respectively patterning of titanium and platinum.

The above mentioned plating of e.g. gold may be an electroplating process. As an alternative to plating, blanket deposition of gold by means of e.g. sputter deposition can be applied. The gold is subsequently masked and etched to form traces. Dry-etching by means of ion milling will enable the formation of trapezium shaped gold traces that can be plated with platinum on the dies walls in a subsequent platinum sputter deposition step.

It is another preferred option it is possible that the high conductive metal is completely encapsulated by the low conductive metal and whereby the high conductive metal is gold, and the low conductive metal is platinum and whereby the all sided encapsulation of gold traces is realized by conducting at least the following process steps:
sputter depositing of a platinum layer;
sputter depositing of gold on the platinum layer and subsequently structure the gold to form traces, preferably with sloped edges;
sputter deposition of platinum; and
patterning of titanium or platinum.

Figure 1:
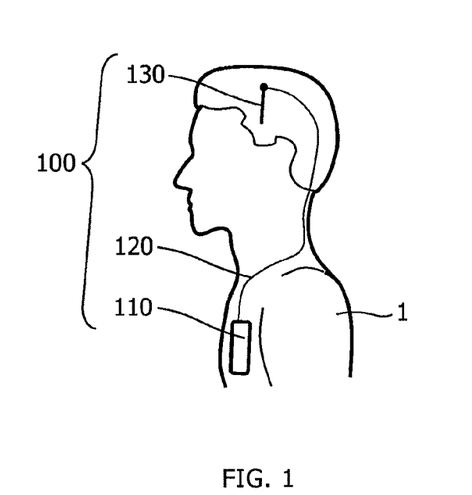
FIG. 1 is a schematic drawing of a neurostimulation system for deep brain stimulation (DBS) in accordance with an exemplary embodiment of the present invention.

An embodiment of a neurostimulation system 100 for deep brain stimulation (DBS) is shown in FIG. 1. The neurostimulation system 100 comprises at least a controller 110 that may be surgically implanted in the chest region of a patient 1, typically below the clavicle or in the abdominal region of a patient 1. The controller 110 can be adapted to supply the necessary voltage pulses. The typical DBS system 100 may further include an extension wire 120 connected to the controller 110 and running subcutaneously to the skull, preferably along the neck, where it terminates in a connector. A DBS lead arrangement 130 may be implanted in the brain tissue, e.g. through a burr-hole in the skull.

Figure 2:
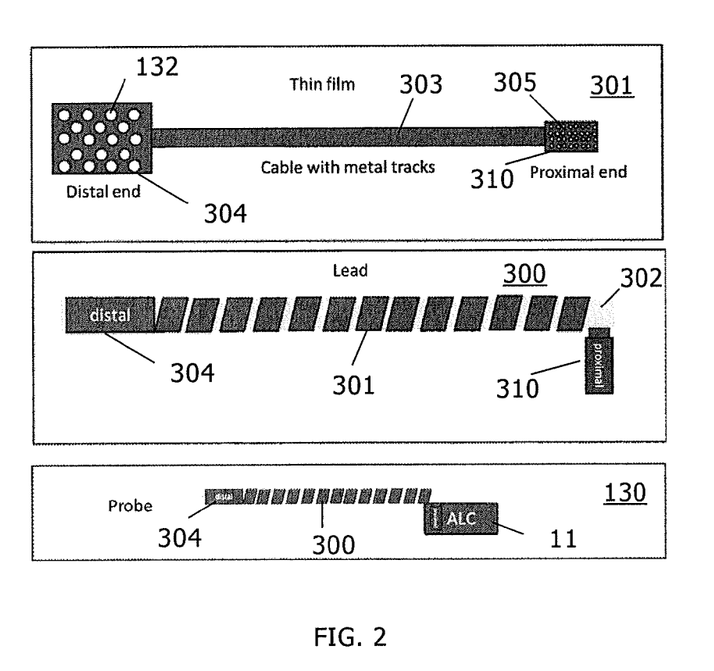
FIG. 2 is a schematic drawing of a probe neurostimulation system for deep brain stimulation (DBS) and its components in accordance with an exemplary embodiment of the present invention.

FIG. 2 further illustrates a typical architecture for a Deep Brain Stimulation probe 130 that comprises a DBS lead 300 and an Advanced Lead Connector element 11 comprising electronic means to address electrodes 132 on the distal end 304 of the DBS lead 300. The lead 300 comprises a carrier 302 for a thin film 301, said carrier 302 providing the mechanical configuration of the DBS lead 300 and the thin film 301. The thin film 301 may include at least one electrically conductive layer, preferably made of a biocompatible material. The thin film 301 is assembled to the carrier 302 and further processed to constitute the lead element 300. The thin film 301 for a lead is preferably formed by a thin film product having a distal end 304, a cable 303 with metal tracks and a proximal end 310. The proximal end 310 of the thin film 301 on the lead 300 is electrically connected to the Advanced Lead Connector element 11. The Advanced Lead Connector element 11 comprises the switch matrix of the DBS steering electronics. The distal end 304 comprises the electrodes 132 for the brain stimulation. The proximal end 310 comprises the interconnect contacts 305 for each metal line in the cable 303. The cable 303 comprises of metal lines (not shown) to connect each distal electrodes 132 to a designated proximal contact 305.

Figure 3:
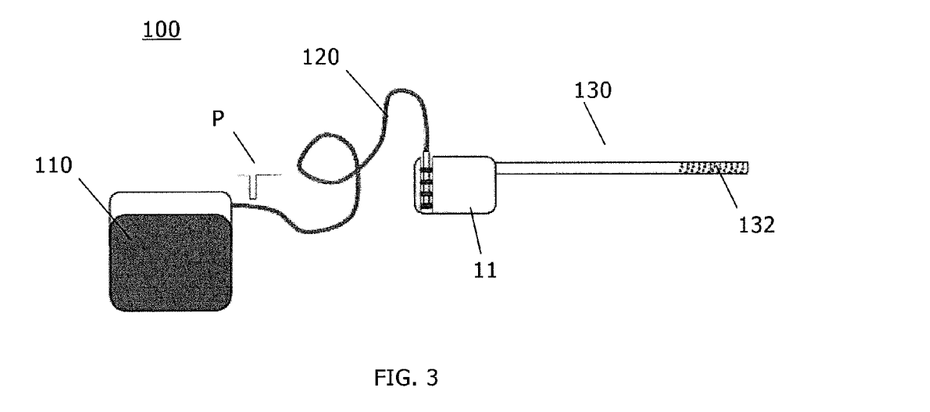
FIG. 3 is a schematic drawing of a probe system in accordance with an exemplary embodiment of the present invention.

FIG. 3 shows schematically and in greater detail an embodiment of a system 100 for brain applications, here for neurostimulation and/or neurorecording as a deep brain stimulation system 100 as shown in FIGS. 1 and 2. The probe system 100 comprises at least one probe 130 for brain applications with stimulation and/or recording electrodes 132, whereby e.g. 64 electrodes 132 can be provided on outer body surface at the distal end of the probe 130. By means of the extension wire 120 pulses P supplied by controller 110 can be transmitted to the Advanced Lead Connector 11. The controller 110 can be an implantable pulse generator (IPG) 110.

According to the present invention, the resistivity of the traces in a thin film 301 are now kept low, typically below 1 to 2 kOhm, to avoid the use of high driving voltages and avoid power losses that negatively influence the battery life.

According to the present invention the resistivity of the traces in thin film lead by introducing a high conductive metal (HCM) such as copper (Cu), aluminium (Al), gold (Au) or silver (Ag) as a conductor may be improved, but without compromising on the compatibility of the metal system by applying an all sided encapsulation of the HCM with a biocompatible metal such as platinum (Pt) or titanium (Ti). Alternatively, also a metal compound such as titanium nitride (TiN) can be used.

Gold, silver and aluminium are not sufficiently biocompatible and are not generally accepted for chronic use in brain probes. All sided encapsulation of the HCM with a biocompatible metal or metal compound/alloy, namely the biocompatible low conductive metal (LCM) may ensure that the tissue is never exposed to the non-biocompatible respectively less-biocompatible HCM.

The encapsulation with biocompatible LCM can be combined with additional encapsulation by ceramics such as SiN, SiOx, Si-Carbide and Alumina as e.g. shown in FIG. 6 and described in detail hereinafter.

These HCM such as gold show much better electrical conductivity. Some of the HCM show e.g. roughly six times better electrical conductivity than platinum. Therefore, HCM layers can be up to six times thinner for the same resistivity.

Standard vacuum thin film deposition technologies, such as sputter deposition, can be applied to deposit the HCM. Alternatively, deposition of the relatively thick layers of these HCMs can be performed by electroplating. The use of electroplated e.g. gold for application in low ohmic traces in implants is already known.

One preferred embodiment of this invention is the use of a HCM with an all sided coating with a low-conductive but biocompatible metal (LCM) while maintaining the benefits of said LCM as a safe metal in brain probe applications. The all sided encapsulation of the HCM by a LCM prevents exposure of the HCM to tissue under all circumstances. The LCM prevents the diffusion of HCM into the thin film encapsulation materials and subsequent diffusion into the brain tissue.

The encapsulation with biocompatible metal can be combined with additional encapsulation by ceramics such as SiN, SiOx, Si-Carbide and Alumina.

Figure 4A:
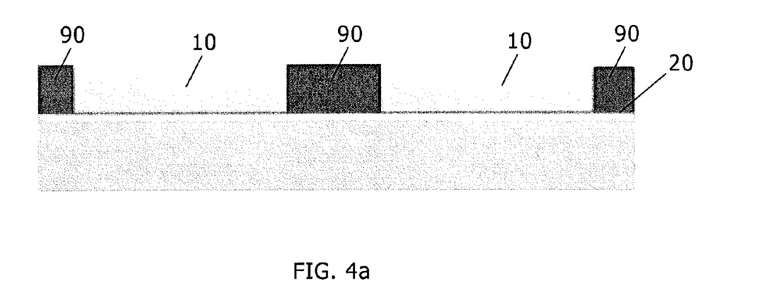
FIGS. 4a and 4b are schematic drawings of steps of a manufacturing process in accordance with an exemplary embodiment of the present invention.
Figure 4B:
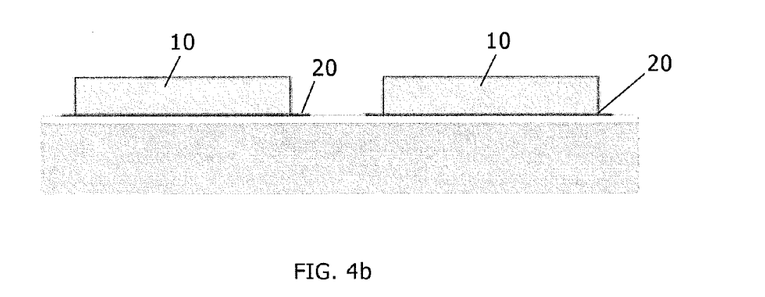

In a preferred embodiment of the invention, the HCM is gold (Au), and the LCM is platinum (Pt). All sided encapsulation of gold traces can be realized by following the following manufacturing process (A) shown in FIGS. 4a and 4b and by conducting the following process steps:

sputter depositing of a platinum 20 layer;
selective gold 10 electroplating of traces on the platinum 20 layer through resist mask 90 to form traces;
patterning of platinum 20; and
platinum 20 electroplating of traces.

An additional titanium layer can be applied to enhance the adhesion of platinum.

Figure 5A:
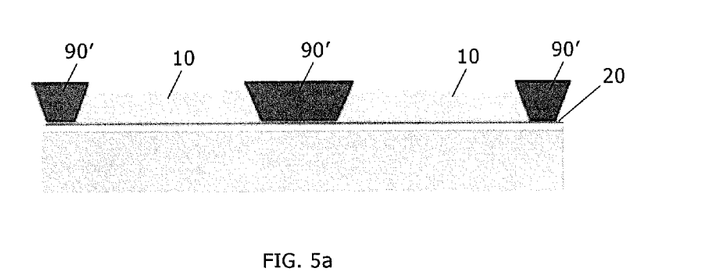
FIGS. 5a and 5b are a further schematic drawing of steps of a manufacturing process in accordance with an exemplary embodiment of the present invention.
Figure 5B:
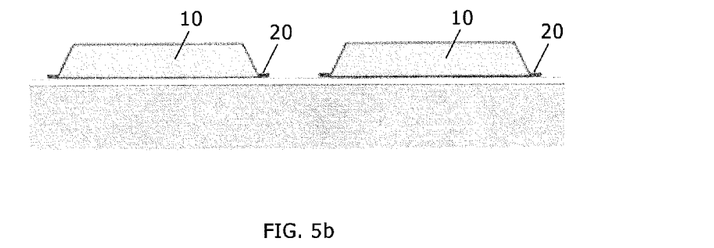

Alternatively, the following manufacturing process (B) can be applied to create all side encapsulated gold traces shown in FIGS. 5a and 5b and by conducting at least the following process steps:

sputter depositing of a platinum layer 20;
selective gold 10 plating on the platinum layer through resist mask 90' with a negative slope to form traces;
sputter deposition of platinum; and
patterning of platinum.

In order to enhance the protection of the metal traces, the traces can have an additional encapsulation by a ceramic material 30 such as SiN, SiOx, SiC or Alumina. This material can be applied in stacks or mixtures. Well known deposition processes that may be used are e.g. Low Pressure Chemical Vapour Deposition (LPCVD), Plasma Enhanced Chemical Vapour Deposition (PECVD) and Atomic Layer Deposition (ALD).

It is possible that only the trace part of the thin film 301 of the lead 300 is equipped with sections with a HCM and a LCM and that the distal electrodes 132 can be manufactured without gold in the thin film layer stack. Thereby and advantageously, any risk of exposure of gold to brain tissue in the distal area of the lead 300 is prevented.

Figure 6:
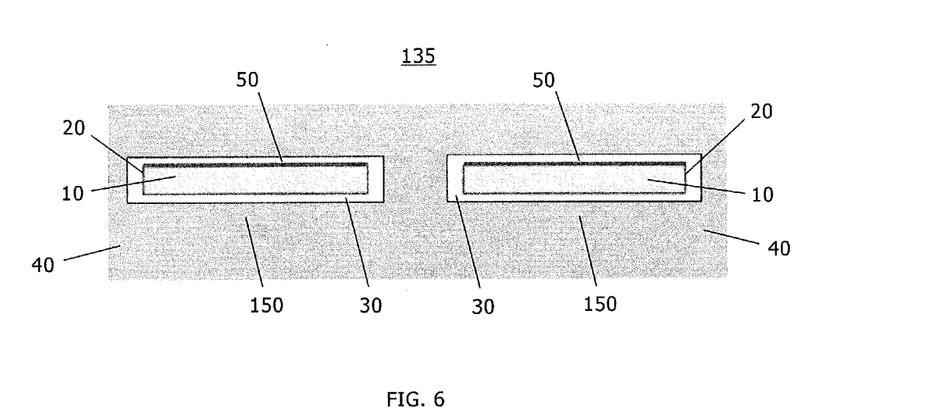
FIG. 6 is a schematic drawing of sections of a thin film of a lead in accordance with an exemplary embodiment of the present invention.

As can be seen in FIG. 6, only the trace part 135 of the thin film 301 of the lead 300 is equipped with sections 150 with a HCM 10, i.e. gold 10 and a LCM 20, i.e. platinum 20. The HCM 10 gold is completely encapsulated by the LCM 20 platinum. An additional pattern 50 is arranged on the LCM 20, whereby the pattern 50 consists of titanium. Additionally, the HCM 10 and the LCM 20 are completely encapsulated by a ceramic material 30, which is in the embodiment shown in FIG. 6 a mixture of SiOx and SiNx. Both sections 150 are fully encapsulated by a flexible and biocompatible polymer 40, which is in this embodiment is Parylene.

In the distal part, sections of the Parylene and the ceramic coating are removed to expose the biocompatible metal. These are the electrode areas. The electrode can consist of the full metal stack, the LCM and the HCM. However, the electrodes are relatively small and the electrical conductivity of the LCM alone is sufficient in this area. Therefore, the distal end of the probe can consist of LCM only.

Explicitly disclosed together with the above described invention is also a method of using a probe 130 comprising a lead 300 according to the present invention for brain applications and treatments, e.g. for DBS. Preferably, at least one thin film 301 according to any of the claims 1 to 10 or at least one thin film 301 for a lead 300 manufactured according to the method of claims 11 to 14 is used.

Furthermore, explicitly disclosed together with the above described invention is also a method of using a deep brain stimulation system 100 according to the present invention for brain applications and treatments, e.g. for deep brain stimulation. Preferably, the deep brain stimulation system 100 of claim 15 is used (see also FIG. 3).

It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

We claim:

1. A medical lead comprising:
   a proximal portion;
   at least one electrode located distal to the proximal portion; and
   an electrically conductive thin film extending from the proximal portion to the at least one electrode, the electrically conductive thin film comprising a metal trace formed of a high conductive metal extending from the proximal portion to the at least one electrode and a low conductive metal that encapsulates all sides of the high conductive metal extending from the proximal portion to the at least one electrode, wherein the low conductive metal comprises platinum, is biocompatible and has a lower electrical conductivity than the high conductive metal, and wherein the metal trace is electrically coupled to the at least one electrode such that electrical signals are conducted via the metal trace between the at least one electrode and a medical device electrically coupled to the medical lead.

2. The medical lead according to claim 1, wherein the electrically conductive thin film includes a ceramic material encapsulating all sides of the low conductive metal extending from the proximal portion to the at least one electrode.

3. The medical lead according to claim 2, wherein the ceramic material comprises at least one of SiN, SiOX, Si-Carbid or Alumina.

4. The medical lead according to claim 2, wherein the electrically conductive thin film comprises a flexible polymer encapsulating all sides of the ceramic material extending from the proximal portion to the at least one electrode.

5. The medical lead according to claim 1, wherein the high conductive metal comprises at least one of gold, copper, aluminum, or silver.

6. The medical lead according to claim 1, wherein the low conductive metal further comprises at least one of titanium, or titanium nitride.

7. The medical lead according to claim 1, wherein the high conductive metal is gold and the low conductive metal is platinum.

8. The medical lead according to claim 1, wherein the electrically conductive thin film comprises titanium on at least a portion of an outer perimeter of the low conductive metal.

9. The medical lead of claim 1, further comprising a carrier material, and wherein the electrically conductive thin film is attached to the carrier material.

10. The medical lead of claim 9, further comprising a polymer material encapsulating the carrier material and the electrically conductive thin film from the proximal portion to the at least one electrode.

11. The medical lead of claim 1, wherein the at least one electrode is defined by an exposed portion of the low conductive metal.

12. The medical lead of claim 1, wherein the low conductive metal encapsulating all sides of the high conductive metal has a substantially uniform composition.

13. The medical lead of claim 1, wherein the platinum is directly on all sides of the high conductive metal.

14. A method comprising manufacturing a medical lead, the lead comprising:
    a proximal portion;
    at least one electrode located distal to the proximal portion; and
    an electrically conductive thin film extending from the proximal portion to the at least one electrode, the electrically conductive thin film comprising a metal trace formed of a high conductive metal extending from the proximal portion to the at least one electrode and a low conductive metal that encapsulates all sides of the high conductive metal extending from the proximal portion to the at least one electrode, wherein the low conductive metal comprises platinum, is biocompatible and has a lower electrical conductivity than the high conductive metal, and wherein the metal trace is electrically coupled to the at least one electrode such that electrical signals are conducted via the metal trace between the at least one electrode and a medical device electrically coupled to the medical lead.

15. The method of claim 14, wherein the electrically conductive thin film includes a ceramic material encapsulating all sides of the low conductive metal extending from the proximal portion to the at least one electrode.

16. The method of claim 15, wherein the ceramic material comprises at least one of SiN, SiOX, Si-Carbide or Alumina.

17. The method of claim 14, wherein the high conductive metal comprises at least one of gold, copper, aluminum, or silver.

18. The method of claim 14, wherein the low conductive metal further comprises at least one of titanium or titanium nitride.

19. The method of claim 14, wherein the high conductive metal is gold and the low conductive metal is platinum.

20. The method of claim 14, wherein the electrically conductive thin film comprises a flexible polymer encapsulating all sides of the low conductive metal extending from the proximal portion to the at least one electrode.

21. The method of claim 14, wherein an additional pattern is arranged on the low conductive metal, and wherein the additional pattern comprises titanium.

22. The method of claim 14, wherein the lead body comprises a carrier material, and wherein the electrically conductive thin film is attached to the carrier material.

23. The method of claim 22, wherein the lead body comprises a polymer material encapsulating the carrier material and the electrically conductive thin film.

24. The method of claim 14, wherein the at least one electrode is defined by an exposed portion of the low conductive metal.

25. The method of claim 14, wherein the low conductive metal encapsulating all sides of the high conductive metal has a substantially uniform composition.

26. The method of claim 14, wherein manufacturing the lead comprises:
sputter depositing a layer of the low conductive metal;
selective plating of the high conductive metal on the low conductive metal through a resist mask to form the metal trace;
patterning of the low conductive metal; and
electroplating of the low conductive metal on exposed portions of the high conductive metal.

27. A deep brain stimulation system comprising:
an implantable pulse generator; and
a medical lead coupled to the implantable pulse generator and configured to deliver electrical stimulation pulses from the implantable pulse generator to a target site via an electrode, the medical lead comprising:
a proximal portion;
at least one electrode located distal to the proximal portion; and
an electrically conductive thin film extending from the proximal portion to the at least one electrode, the electrically conductive thin film comprising a metal trace formed of a high conductive metal extending from the proximal portion to the at least one electrode and a low conductive metal that encapsulates all sides of the high conductive metal extending from the proximal portion to the at least one electrode, wherein the low conductive metal comprises platinum, is biocompatible and has a lower electrical conductivity than the high conductive metal, and wherein the metal trace is electrically coupled to the at least one electrode such that electrical signals are conducted via the metal trace between the at least one electrode and a medical device electrically coupled to the medical lead.

28. The deep brain stimulation system of claim 27, wherein the platinum is directly on all sides of the high conductive metal.

* * * * *